(12) United States Patent
Ossipov et al.

(10) Patent No.: US 9,636,216 B2
(45) Date of Patent: May 2, 2017

(54) INJECTOR CARTRIDGE WITH IMPROVED LUBRICITY

(71) Applicant: STAAR SURGICAL COMPANY, Monrovia, CA (US)

(72) Inventors: Alexei Ossipov, Laguna Niguel, CA (US); Thomas R. Paul, Westlake Village, CA (US)

(73) Assignee: STAAR Surgical Company, Monrovia, CA (US)

( * ) Notice: Subject to any disclaimer, the term of this patent is extended or adjusted under 35 U.S.C. 154(b) by 0 days.

(21) Appl. No.: 14/254,746

(22) Filed: Apr. 16, 2014

(65) Prior Publication Data

US 2014/0316425 A1    Oct. 23, 2014

Related U.S. Application Data

(60) Provisional application No. 61/814,100, filed on Apr. 19, 2013, provisional application No. 61/947,925, filed on Mar. 4, 2014.

(51) Int. Cl.

| | |
|---|---|
| *A61F 2/16* | (2006.01) |
| *B05D 7/02* | (2006.01) |
| *B05D 1/18* | (2006.01) |
| *C08J 7/12* | (2006.01) |
| *B05D 3/02* | (2006.01) |
| *B05D 3/10* | (2006.01) |

(52) U.S. Cl.
CPC .............. *A61F 2/1675* (2013.01); *B05D 1/18* (2013.01); *B05D 7/02* (2013.01); *C08J 7/12* (2013.01); *B05D 3/0272* (2013.01); *B05D 3/101* (2013.01); *C08J 2369/00* (2013.01)

(58) Field of Classification Search
CPC .......... B32B 9/00; B32B 17/00; A61F 2/1675
USPC ....................................................... 428/410
See application file for complete search history.

(56) References Cited

U.S. PATENT DOCUMENTS

4,529,657 A  *  7/1985  Franz ...................... C03C 17/28
                                                      427/301
4,731,079 A     3/1988  Stoy
(Continued)

FOREIGN PATENT DOCUMENTS

JP    2000514333       10/2000
JP    2005002377   *    1/2005   ............. B32B 17/00

OTHER PUBLICATIONS

Greenwall, Glass Versus Polycarbonate, Oct. 2012, http://www.greenwallsolutions.com/installation/glass-vs-polycarbonate/.*

(Continued)

*Primary Examiner* — Dah-Wei D Yuan
*Assistant Examiner* — Andrew Bowman
(74) *Attorney, Agent, or Firm* — Rutan & Tucker LLP; John K. Fitzgerald

(57) ABSTRACT

An inorganic-organic hybrid coating applied to a polymer and method for forming same to provide improved hydrophilicity and lubricity to the surface of the polymer. The hydrophilic coating is on the order of one micron thick, as is formed by activating the surface of the polymer, reacting the activated surface of the polymer with a Lewis acid metallic composition, and then quenching the coating in salt solution having a pH>7.2 at a temperature above the glass transition temperature ($T_g$) of the polymer.

8 Claims, 14 Drawing Sheets

(56) References Cited

U.S. PATENT DOCUMENTS

| | | | |
|---|---|---|---|
| 5,331,027 | A | 7/1994 | Whitbourne |
| 5,716,364 | A | 2/1998 | Makker et al. |
| 5,942,277 | A | 8/1999 | Makker et al. |
| 6,083,230 | A | 7/2000 | Makker et al. |
| 6,238,975 | B1 | 5/2001 | Fliesler et al. |
| 6,398,788 | B1 | 6/2002 | Makker et al. |
| 2005/0147735 | A1 | 7/2005 | Lowery et al. |
| 2009/0112313 | A1 | 4/2009 | Mentak |
| 2011/0046634 | A1 | 2/2011 | Rathert |

OTHER PUBLICATIONS

PCT International Search Report, Apr. 17, 2014, 3 pages, PCT/US2014/034501.
PCT Written Opinion of the International Searching Authority, Sep. 9, 2014, 4 pages, PCT/US2014/034501.

\* cited by examiner

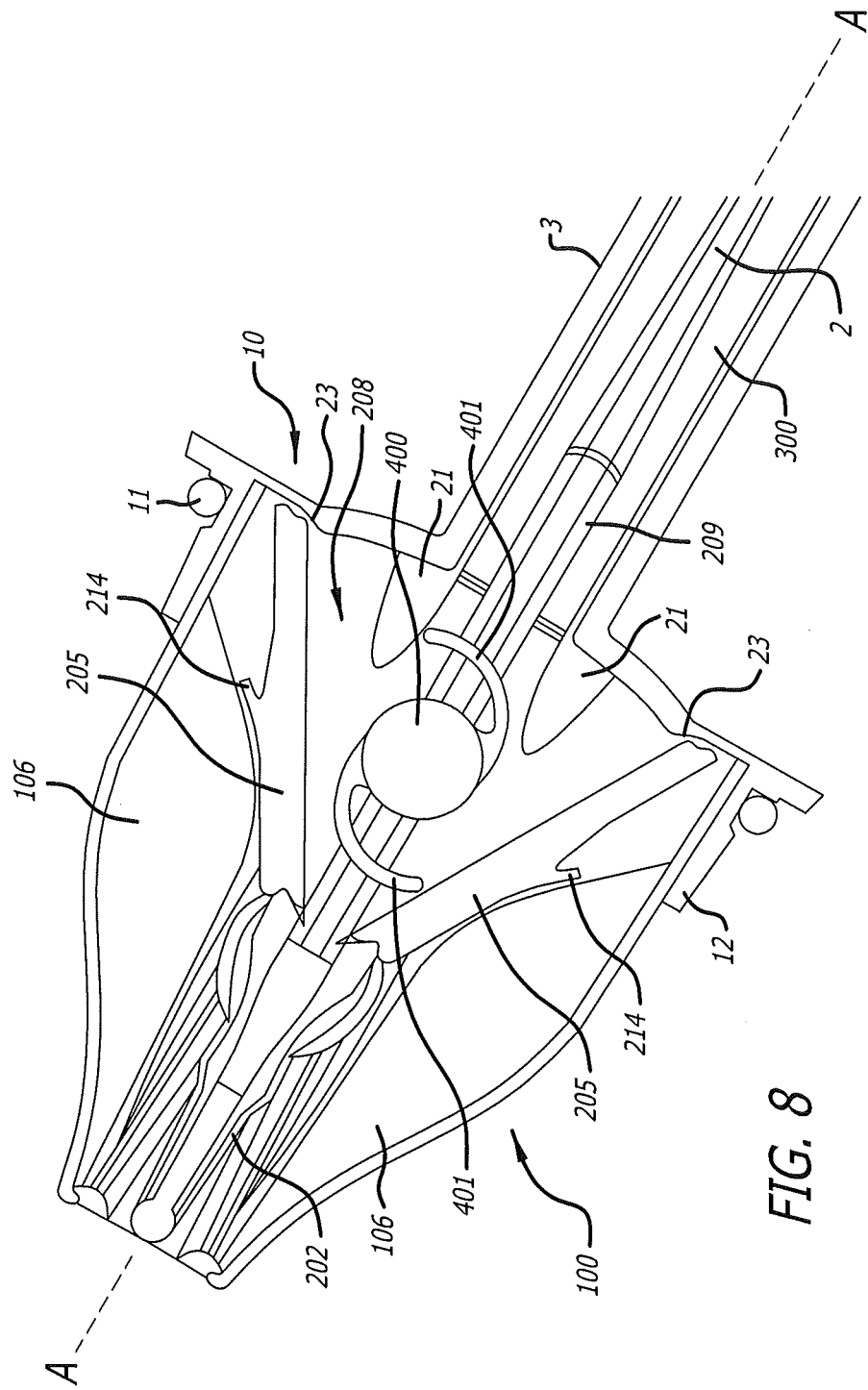

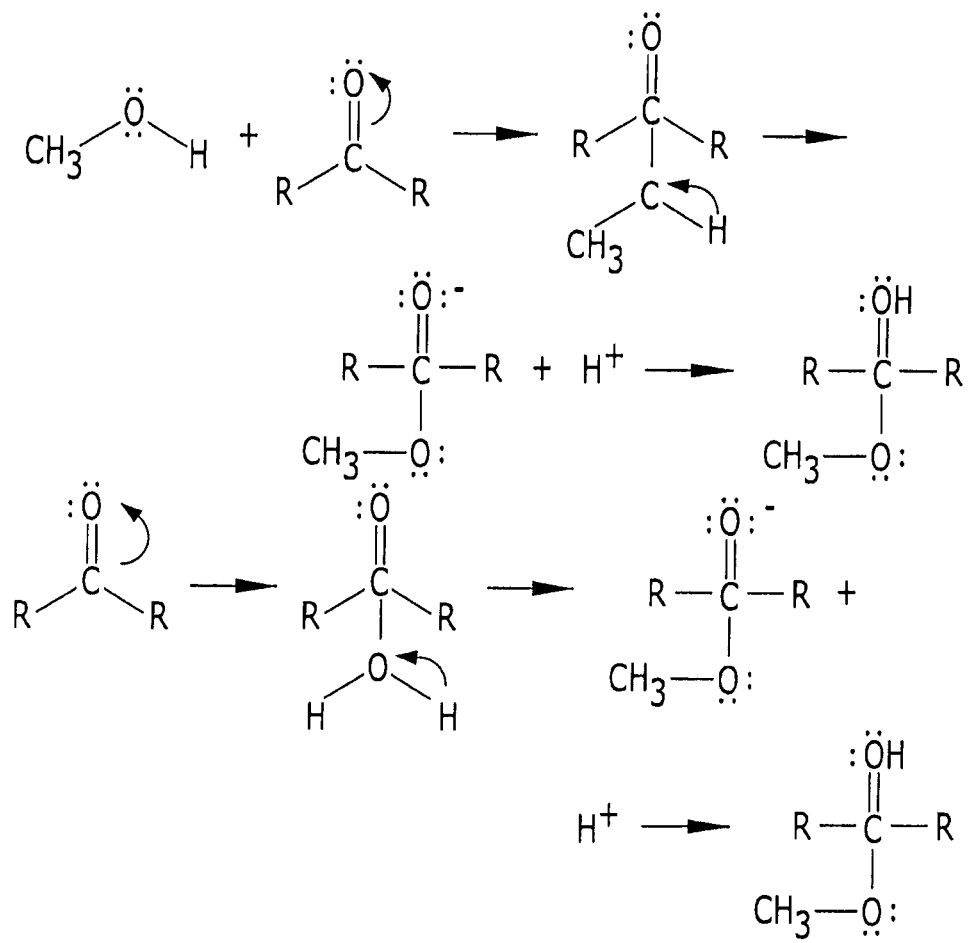
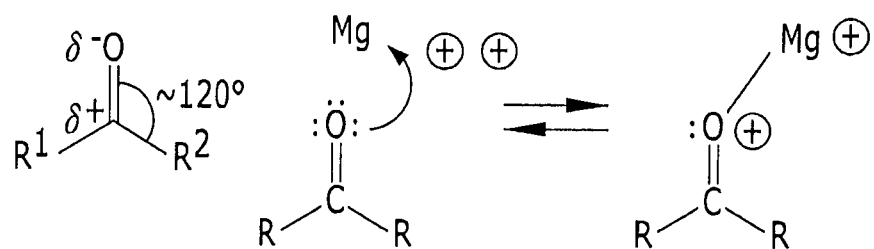
FIG. 16

INJECTOR CARTRIDGE WITH IMPROVED LUBRICITY

CROSS-REFERENCES TO RELATED APPLICATIONS

This application claims priority from U.S. Provisional Application No. 61/814,100, filed Apr. 19, 2013 and U.S. Provisional Application No. 61/947,925, filed Mar. 4, 2014 incorporated by reference herein in their entireties.

BACKGROUND

The invention relates to injector cartridges for intraocular lens injection into an eye of a patient, and more specifically to methods for improving the wettability of hydrophobic plastic surfaces of medical devices without providing or forming a separate coating of a lubricious agent on the surface of the medical device.

The human eye in its simplest terms functions to provide vision by transmitting and refracting light through a clear outer portion called the cornea, and further focusing the image by way of lens onto the retina at the back of the eye. The quality of the focused image depends on many factors including the size, shape and length of the eye, and the shape and transparency of the cornea and lens.

When trauma, age or disease cause the lens to become less transparent, vision deteriorates because of the diminished light which can be transmitted to the retina. This deficiency in the lens of the eye is medically known as a cataract. The treatment for this condition is surgical removal of the lens and implantation of an intraocular lens (IOL).

While early IOLs were made from hard plastic, such as polymethylmethacrylate (PMMA), soft foldable IOLs made from silicone, soft acrylics and hydrogels have become increasingly popular because of the ability to fold or roll these soft lenses and insert them through a smaller incision. Several methods of rolling or folding the lenses are used. One popular method is an injector cartridge that folds the lenses and provides a relatively small diameter lumen through which the lens may be pushed into the eye, usually by a soft tip plunger. Commonly used injector cartridge design are illustrated in, for example, U.S. Pat. No. 4,681,102 (Bartell), U.S. Pat. Nos. 5,494,484 and 5,499,987 (Feingold) and U.S. Pat. Nos. 5,616,148 and 5,620,450 (Eagles, et al.), the entire contents of which are incorporated herein by reference.

One problem that exists for typical currently available cartridges is that the IOL may stick to the inner surface of the cartridge when the an attempt is made to inject the IOL into an eye by moving the lens along a pathway in the cartridge that is configured to fold the lens as it traverses the pathway from a position where the lens is unfolded to the nozzle of the injector for insertion into the eye. In some cases, viscoelastic material is inserted into the injector prior to pushing the lens through the lens delivery and folding pathway. In other case, the surface of the injector is modified in some fashion so as to render it more lubricious. For example, an additive may be added to the material from which the injector is formed to provide lubricity.

Alternatively, a lubricious coating may be added to the interior surface of the injector. However, such a coating may transfer to the lens and being carried into the eye. Additionally, most coating cannot retain their lubricity and physical integrity during steam sterilization in the presence of water, or avoid generating particles or dissolved coating which contaminates the storage media in which the lens is stored after packaging.

Accordingly, what has been needed and heretofore unavailable is a lens cartridge that can be modified to attain an essentially permanent increase in lubricity to facilitate implantation of an IOL into the eye. Such a modification would be stable in the presence of a storage media, and would be able to withstand steam sterilization, particularly where the modification is applied to a cartridge in which a lens is loaded, an aqueous storage media is added to the cartridge to maintain the lens in an aqueous medium, and then the entire package is steam sterilized. In this manner the IOL injector cartridge may also be used as a shipping case. The present invention fulfills these, and other needs.

SUMMARY OF THE INVENTION

In its most general aspect, the invention includes an inorganic-organic hybrid coating applied to a polymer and method for forming same to provide improved hydrophilicity and lubricity to the surface of the polymer. The hydrophilic coating is on the order of one micron thick, as is formed by activating the surface of the polymer, reacting the activated surface of the polymer with a Lewis acid metallic composition, and then quenching the coating in salt solution having a pH>7.2 at a temperature above the glass transition temperature ($T_g$) of the polymer.

In another aspect, the invention includes a method for improving the lubricity of a polycarbonate construct, comprising: activating the surface of a polycarbonate construct by placing the construct in an activation solution and heating the solution at a selected activation temperature for a selected activation time; drying the activated construct; coating the activated construct by immersing the construct in a coating solution and heating the solution at a selected coating temperature for a selected coating time; drying the coated construct; and quenching the coated construct by immersing the coated construct in a quenching solution contained within an autoclavable vessel and autoclaving the coated construct for a selected autoclaving time at a selected autoclaving temperature.

In one alternative aspect, the activation solution is 100% anhydrous Ethanol. In another alternative aspect, the coating solution is a 2.0 molal solution of $MgCl2$ in DI water. In still another alternative aspect, the quenching solution is balanced saline solution with a pH of 8.6-8.7.

In yet another aspect, the invention includes a polycarbonate construct having a surface coating formed using the method described above. In an alternative aspect, the polycarbonate is a polymer blend or co-polymer. In still another alternative aspect, the polycarbonate construct comprises a lens holding portion of an injector configured to deliver an intraocular lens into an eye.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 8 is a sectional view illustrating an intraocular lens disposed within the lens support, according to an embodiment of the invention.

FIG. 16 is a schematic representation illustrating nucleophilic additions to a carbon-oxygen double bond in one embodiment of the invention.

DETAILED DESCRIPTION OF THE PREFERRED EMBODIMENTS

Figure 1:
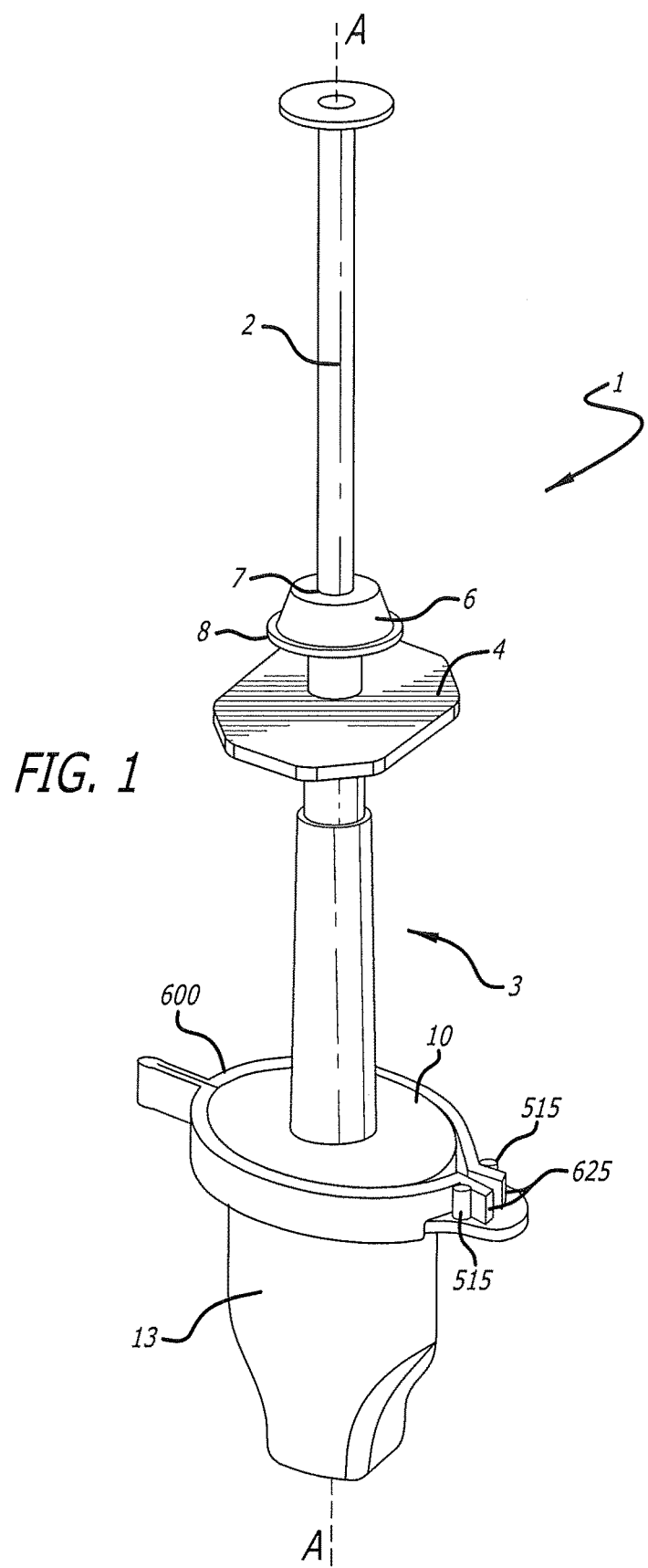
FIG. 1 is a perspective side view of an improved injector having an end cap, an injector body, a plunger, according to an embodiment of the invention.
Figure 2:
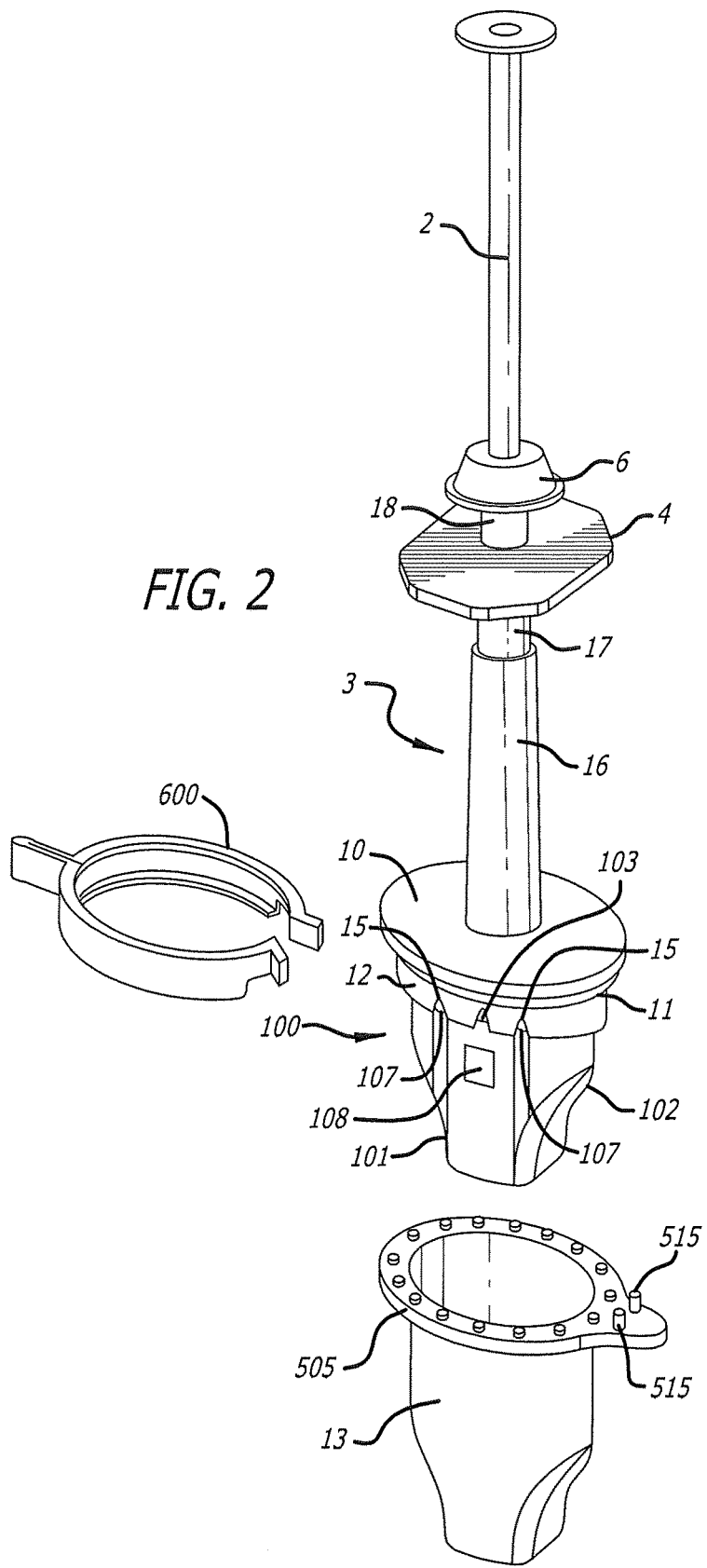
FIG. 2 is a partial view of the injector of FIG. 1 where the end cap has been removed, showing a support guide.

Referring now to the drawings in detail, in which like reference numerals indicate like or corresponding elements among the several figures, there is shown in FIG. 1 an embodiment of a preloaded injector. The injector 1 comprises a plunger 2, extending along a longitudinal axis corresponding to the injection axis A, within a hollow cylindrical injector body 3. In the example of FIGS. 1 and 2, the injector body 3 includes an octagonal shaped finger tab 4 which is intended to provide a holding point to facilitate operation of the plunger 2 during usage of the injector to inject a deformable intraocular lens into an eye of a patient. Different configurations of the injector body 3 and finger tab 4 are also possible as long as the injector body 3 is provided with means against which the fingers of a user can bear.

The injector body 3 is closed at its proximal end by an end piece 6 comprising an opening 7 in which the plunger 2 is introduced and guided. The end piece 6 has a sleeve portion 8 arranged to be fixed by snap-fit into the proximal end of the injector body 3. A first toric joint seal 9 (FIG. 3) is accommodated in the end piece 6 in order to fluidly seal the end piece 6 on the injector body 3 and the opening 7 with the plunger 2 passing through it. The toric joint seal 9 may be formed of any flexible elastomeric material.

At its distal end, or at the end opposite to the end piece 6, the injector body 3 comprises an oval-shaped flange portion 10 extending essentially perpendicular to the injection axis A. Flange 10 comprises a collar portion 12 (FIG. 2), extending in the axial direction from part 10. Other configurations of the flange 10 are also possible. For example, flange 10 can have a circular, an elliptical or a rectangular shape and can be supported on the injector body 3 with support elements (not shown).

In one embodiment of the invention, the injector body 3 comprises a first portion 16 having a first internal diameter and extending from the flange 10 to a second portion 17 having a second internal diameter that is smaller than the first internal diameter (FIG. 2). The injector body 3 also comprises a third portion 18, having an internal smaller than the one of the second portion 17, and extending between the second portion 17 and the end piece 6.

In FIG. 1, the injector 1 comprises an end cap 13 configured to fit over the collar portion 12 and engage with flange 10 to hold proximal end of the injector in a sealed arrangement, allowing for fluid to be introduced into a cavity of the end cap 13 to form a fluid reservoir and to maintain the fluid within the reservoir formed by the cooperation of the end cap and flange 10. A second toric joint seal 11 (FIG. 2) placed around the outer wall of the collar portion 12 insures the fluid tightness between the end cap 13 and flange 10.

Figure 10:
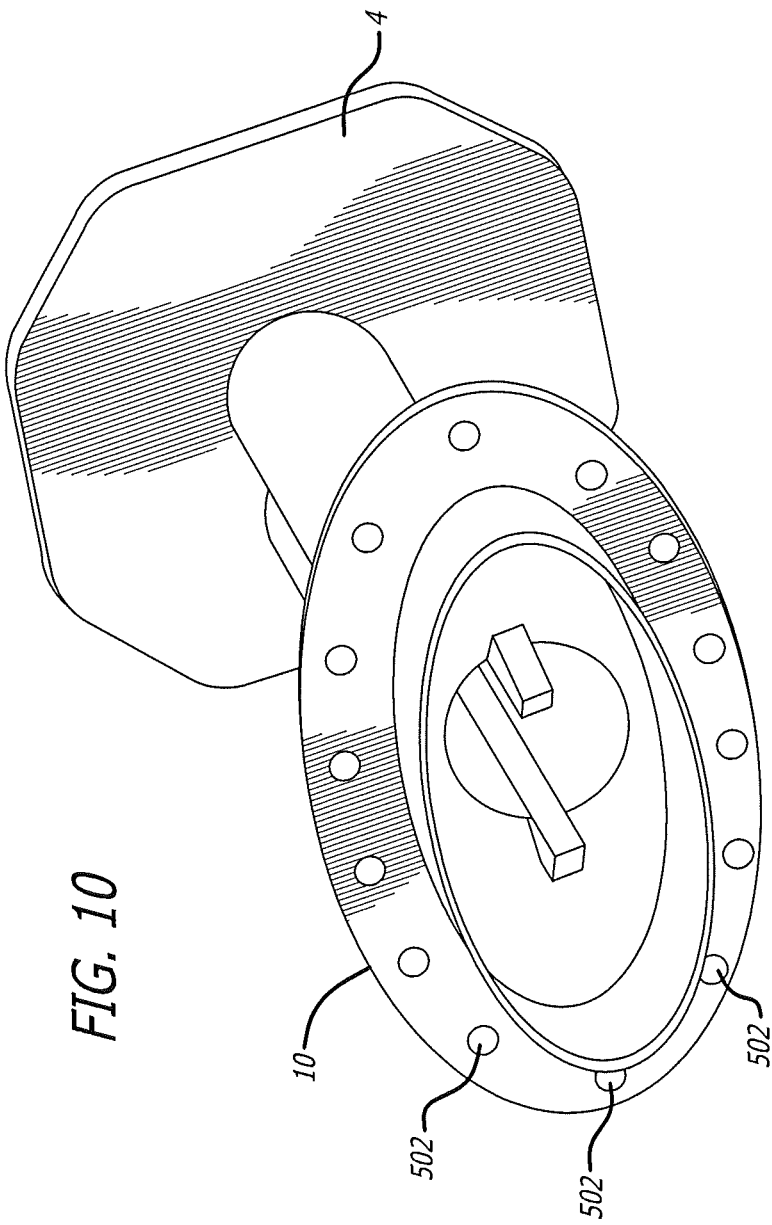
FIG. 10 illustrates a view of the injector of an embodiment of the invention, viewed from its proximal end showing details modifications to the proximal end to enhance retention of fluid within the injector.
Figure 11:
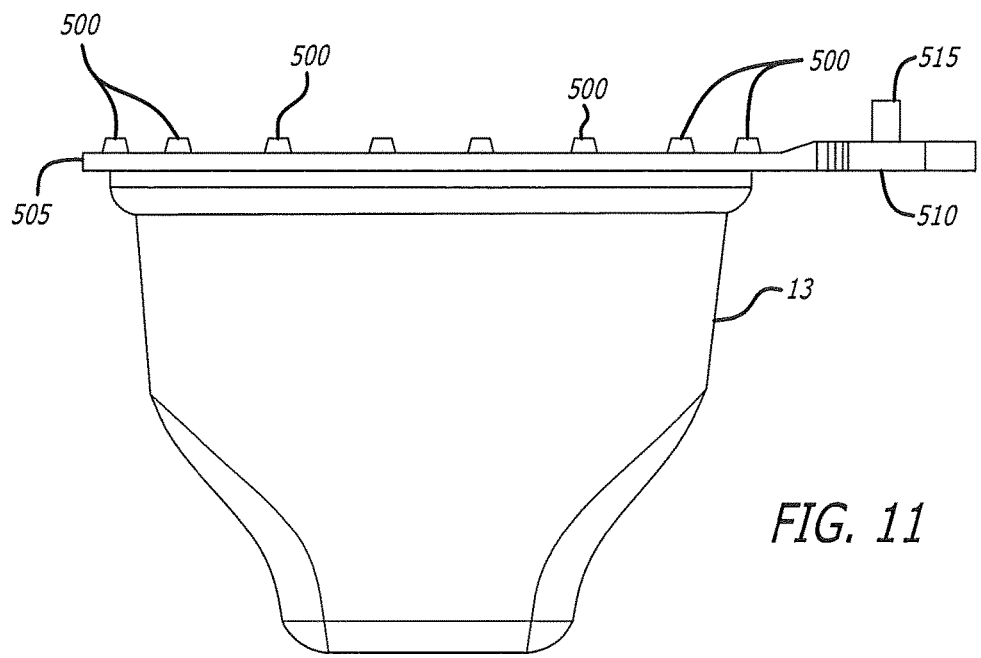
FIG. 11 is a side view of an end cap of embodiment of FIG. 10.

Referring now to FIGS. 10 and 11, details of and embodiment of the flange 10 and end cap 13 are shown that improve the ability to maintain fluid within the reservoir formed by flange 10 and end cap 13, even when the injector assembly is sterilized using an autoclave. As one skilled in the art will understand, when the injector assembly is steam sterilized, pressure may build up within the reservoir that causes fluid to leak from the reservoir, either during the sterilization process, or afterwards when the injector is stored. The inventors have observed that reservoir integrity and fluid retention may be improved by incorporating seal posts 500 (FIG. 11) disposed around a top edge 505 of the cap 13 configured to be received by and engage with seal holes or indents 502 disposed on the distal side of flange 10 (FIG. 10). Seal holes 502 may extend completely through flange 10, or they may be formed only as indents of partial holes disposed on the distal side of flange 10, having a depth sufficient to receive the seal posts 500 such that the distal side of flange 10 mates with the top edge of cap 13 to form a fluid seal.

Figure 12:
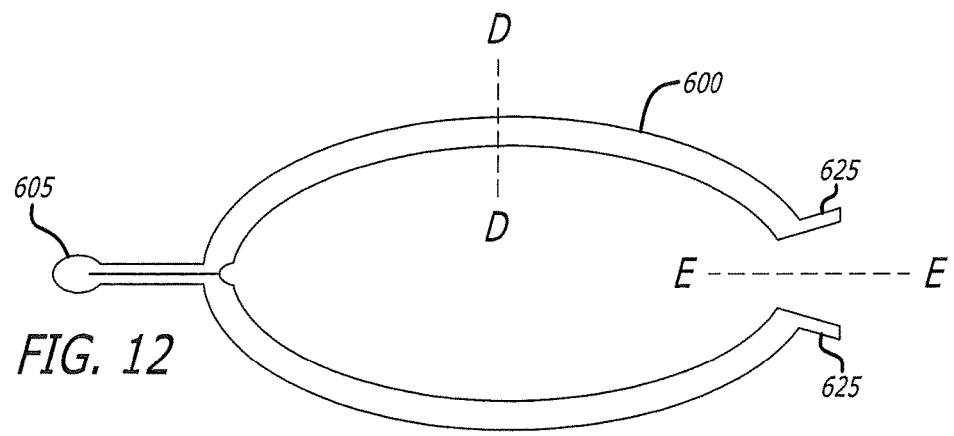
FIG. 12 is a top view of an embodiment of a clamp used to hold the end cap of FIG. 11 onto the proximal end of the injector of FIG. 10.
Figure 13:
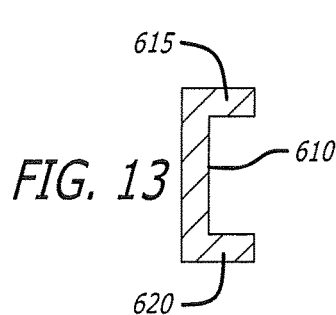
FIG. 13 is a partial view of the clamp of FIG. 12 taken along the line D-D showing the "U shaped" construction of the clamp.

Referring now to FIG. 12, there is shown a locking clamp 600 configured to cooperate with flange 10 and the top edge 505 of cap 13. FIG. 13 is a sectional view taken along line D-D of FIG. 12 showing the arrangement of one embodiment of locking clamp 600. Clamp 600 is formed to have an approximate "C" shape that engages edges of flange 10 and top edge 505 of the cap 13. To accomplish this, clamp 600 has an upper lip 615 and a lower lip 620 connected by a web 610, forming a "U" shaped channel. The spacing between upper lip 615 and lower lip 620 is configured to accept an edge of flange 10 and the top edge 505 of cap 13 between the upper and lower lips.

Referring again to FIGS. 11 and 12, cap 13 includes a tab 510 that includes one or more posts or pins 515 configured to engage ends 625 of clamp 600. In one embodiment, each end 625 of clamp 600 is held in place by a post 515 mounted on a top side of the top edge 505 of cap 13. Those skilled in the art will understand that other embodiments are possible, such as an embodiment where the post 515 is replaced by a tab or other structure capable of holding end 625 of clamp 600 in place.

Figure 14:
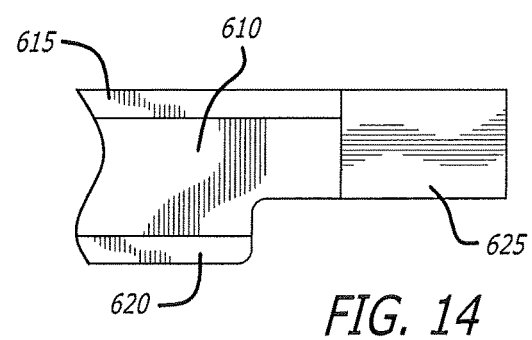
FIG. 14 is a partial view of the clamp of FIG. 12 taken along the line E-E showing the details of a distal end portion of one side of the claim configured to engage a pin of the embodiment of FIG. 11.

FIG. 14 is a partial view taken along line E-E of FIG. 12 that shows how each of the proximal ends 625 of clamp 600 are configured to engage pins 515 of cap 13. As shown, proximal ends 625 are formed in a tab shape that is defined by partially cutting away lower edge 620 and a portion of web 610. This construction provides a relief that allows the end 625 to pass over the top side of flange 10 and engage pin 515. When both ends 625 engage both pins 515, the clamp is securely held in place, and securely holds flange 10 and cap 13 together. In this manner, the joint between the injector and the cap is made secure and is capable of withstanding pressure changes within the cap during sterilization that could lead to fluid loss from the reservoir within the cap.

Clamp 600 may be made of any material that is suitable for use with the injector system such that it is able to withstand autoclaving or methods of sterilization. Clamp 600 must also be sufficiently flexible to allow placement of clamp 600 around the flange and cap without breakage. In the embodiment shown in FIG. 12, clamp 600 includes hinge 605 formed between the two arms of the clamp. Hinge 605 allows the arms of the clamp to be opened for placement about the edges of the flange and cap. Hinge 605 may be an actual hinge arrangement, or the clamp may be formed from a material that can be repeatedly articulated, with hinge 605 being formed from a shape that facilitates such articulation in a "living hinge" arrangement well known in the art.

Figure 3:
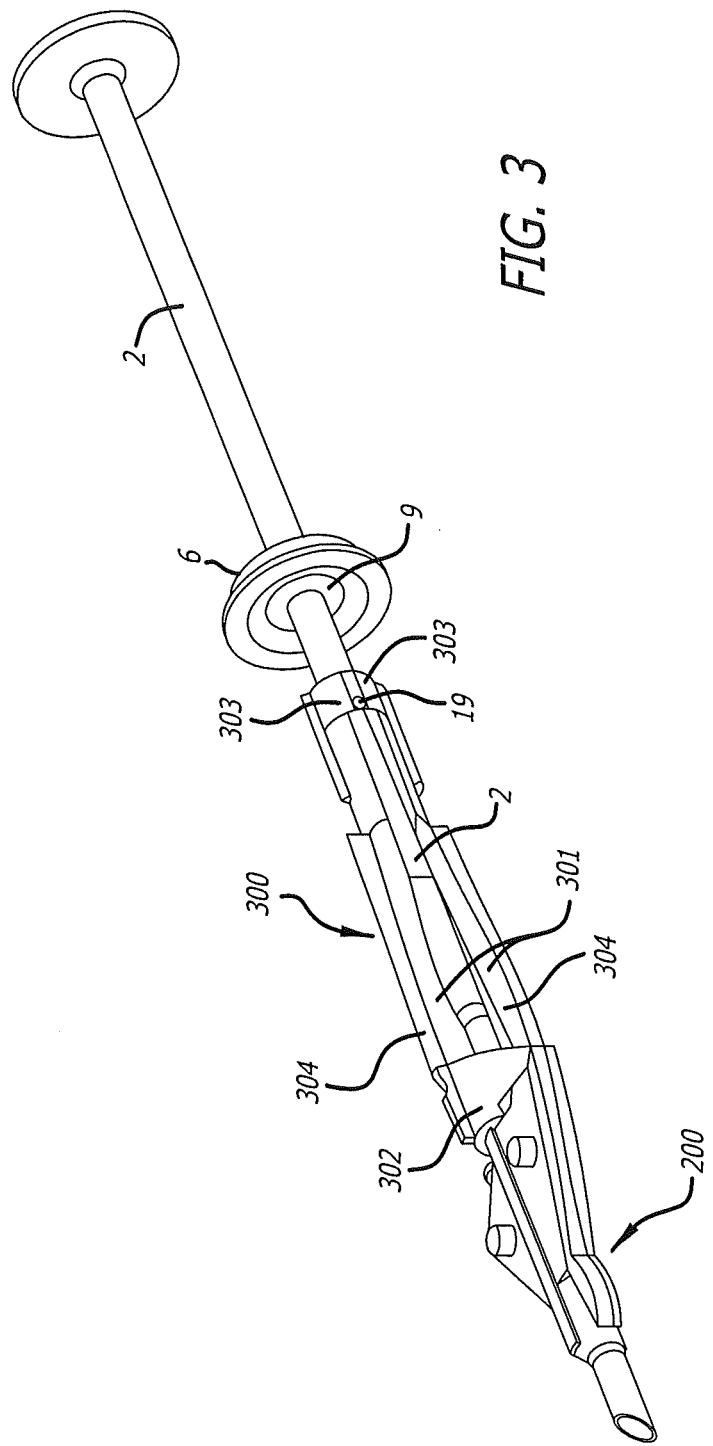
FIG. 3 is another partial view of the injector where end cap, injector body, and support guide have been removed, showing a lens support, a plunger guide and a plunger.

Referring again the FIGS. 1-3, the injector 1 also comprises a lens compartment consisting of a support guide 100 and a lens support 200 (FIG. 3). FIG. 2 shows the injector 1 where the end cap 13 has been removed from the injector body 3, showing the support guide 100 fixed on the flange 10. The support guide 100 is an open hollow structure having side walls defining a tapered internal shape, a narrower, truncated support guide distal end 101, and a wider proximal end 102 having an oval section, or any section conformal with the internal periphery of the collar portion 12. The support guide 100 can be mounted and fixed on the flange 10 by press-fitting its proximal end 102 within the internal periphery of the 5 collar portion 12.

As shown in FIG. 2, the support guide 100 contains a guiding pin 103 fitted in a corresponding indentation 15 in the collar portion 12, insuring a better positioning and fixation of the support guide 100 on the flange 10. Holes 107 are provided in the support guide 100 in order to allow for the introduction of a viscoelastic solution within the lens support 200 as will be 10 explained below. Holes 107 are accessible through indentations 15 let into the collar portion 12.

Support guide 100 also includes an inspection window 108 disposed on a surface of support guide 100. Inspection window 108 provides for viewing the positioning and state of an intraocular lens 400 disposed within an internal support cavity 208 (FIG. 8) when the intraocular lens is loaded into the injector.

In one embodiment of the invention, the injector body 3 is fabricated in one piece with an injection plastic molding process. The material used for the injector body and cap 13 should be sterilizable using various processes, include steam sterilization. The material used for cap 13 may be opaque or clear. Alternatively, cap 13 may be formed in such a manner that a portion of the cap is opaque and a portion of the cap is clear, forming a window, allowing visualization of the portion of the injector and the lens mounted in the injector, as well as the level of any fluid within the reservoir formed by flange 10 and cap 13, that is placed within cap 13.

FIG. 3 depicts another partial view of the injector 1 from which the injector body 3, the end cap 13, and the support guide 100, have been removed. In this view, the plunger 2 extending between the end piece 6, with its toric joint seal 9, and the lens support 200, placed underneath the support guide 100. Also visible in FIG. 3 is a plunger guide 300, disposed 20 within the injector body 3 and extending between the internal wall of the injector body 3 and the plunger 2. The plunger guide 300 comprises a pair of flexible legs 301 of hollow semi-oval shape, the legs 301 being connected on the distal side of the plunger guide 300, or on the side of the lens support 200, by a connecting portion 302 integrally formed with the legs 301. The legs 301 each 25 comprise a protruding stop piece 303 at their respective free ends.

In FIG. 3, the legs 301 are shown in an unstressed open position allowing the plunger 2 to move axially within the plunger guide 300. The plunger guide 300 also comprises two opposite ribs 304, extending along its whole length. The ribs 304 are guided in corresponding grooves (not shown) provided 30 in the internal wall of the injector body 3, when the plunger guide 300 is inserted within the injector body 3, and used to orient radially and guide axially the plunger guide 300 within the injector body 3.

Figure 4:
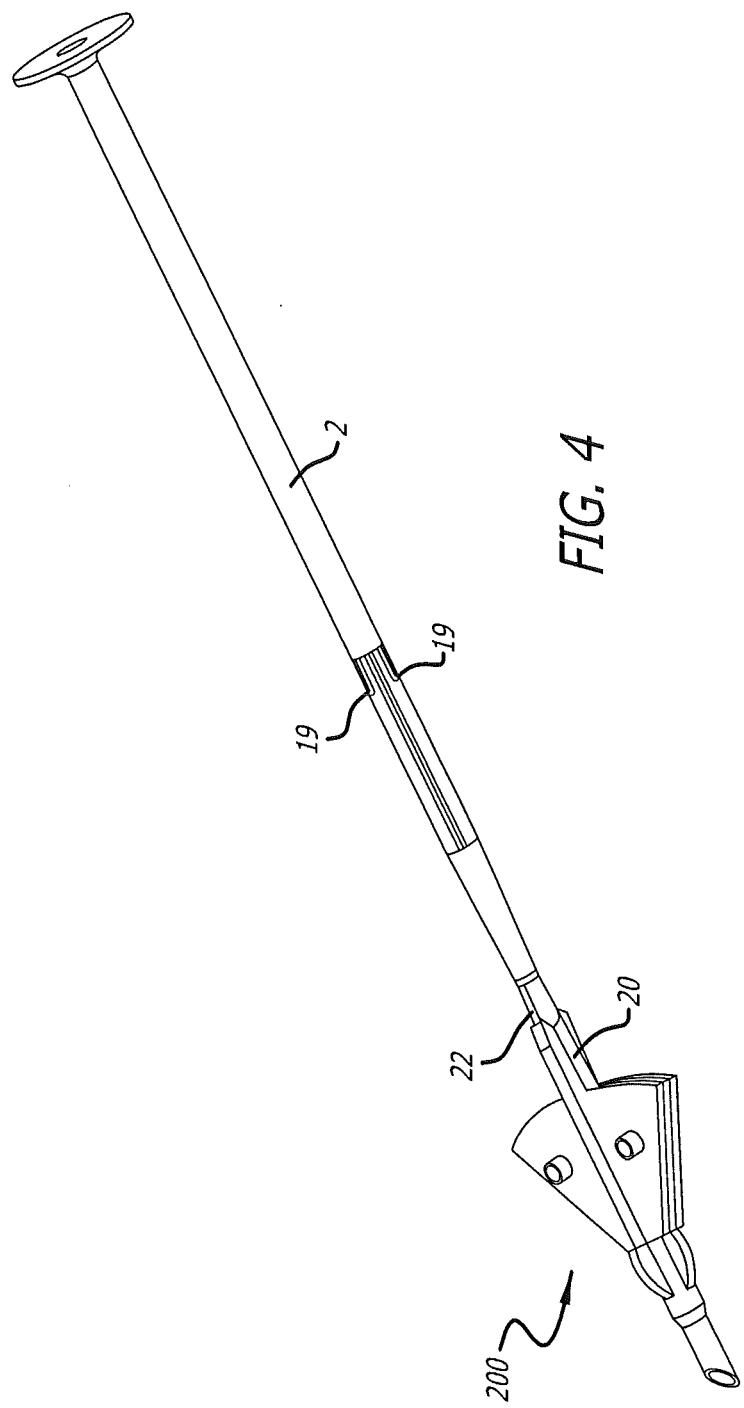
FIG. 4 depicts an isolated view of a plunger and a lens support.

FIG. 4 shows a view of the plunger 2 with the lens support 200 disposed at the distal end 22 of the plunger 2. The plunger 2 preferably has an elliptical or ovoid section but can have any other suitable section shape such as a circular, square or rectangular section. The plunger 2 also comprises clipping means. In the embodiment shown in FIG. 4, the clipping means are two snap hooks 19 that are oppositely disposed on the plunger 2, each at a position corresponding to that one of a stop piece 303 of the plunger guide 300.

Figure 5:
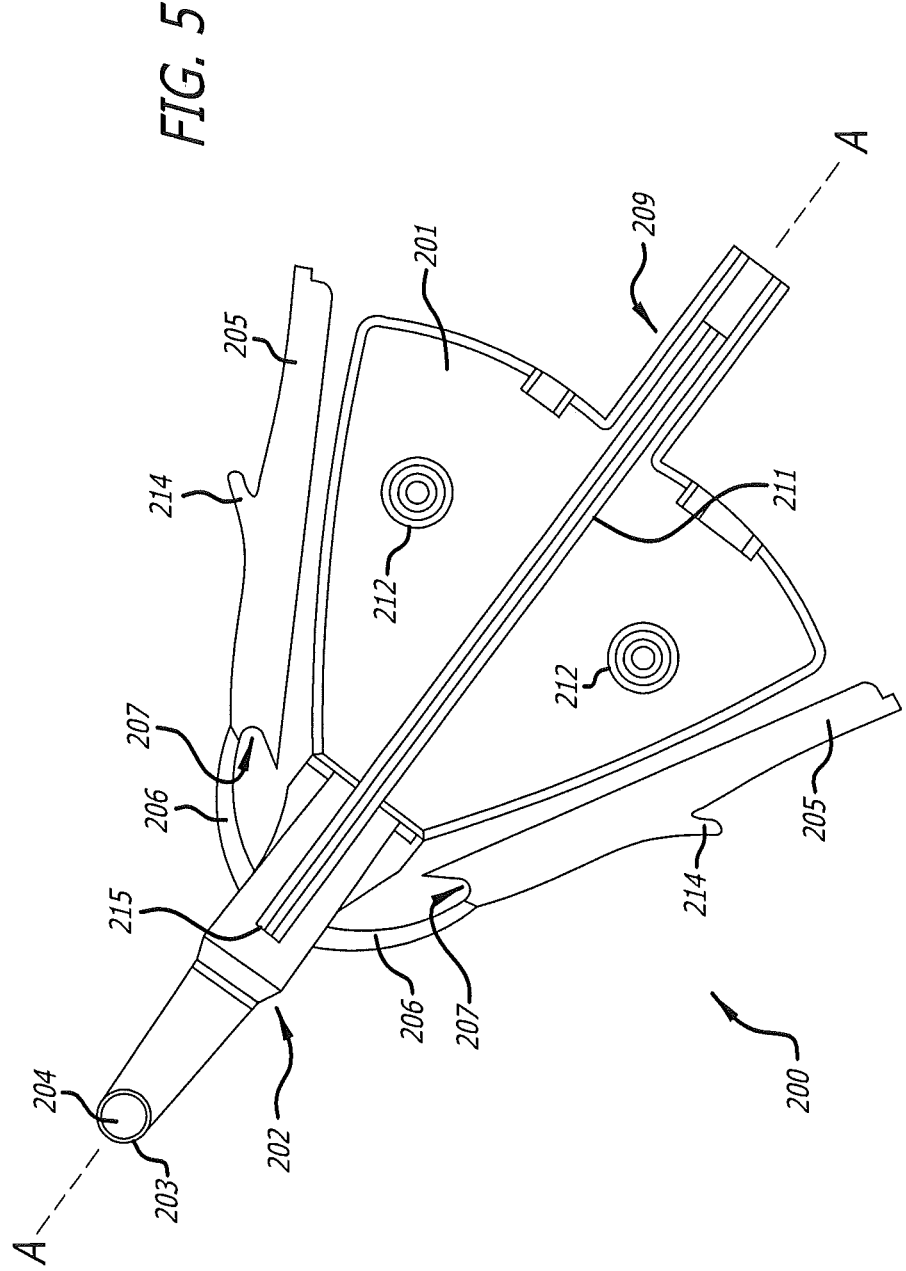
FIG. 5 is an isolated view of a lens support with wedge plate, a pair of folding members and an injection nozzle.
Figure 6:
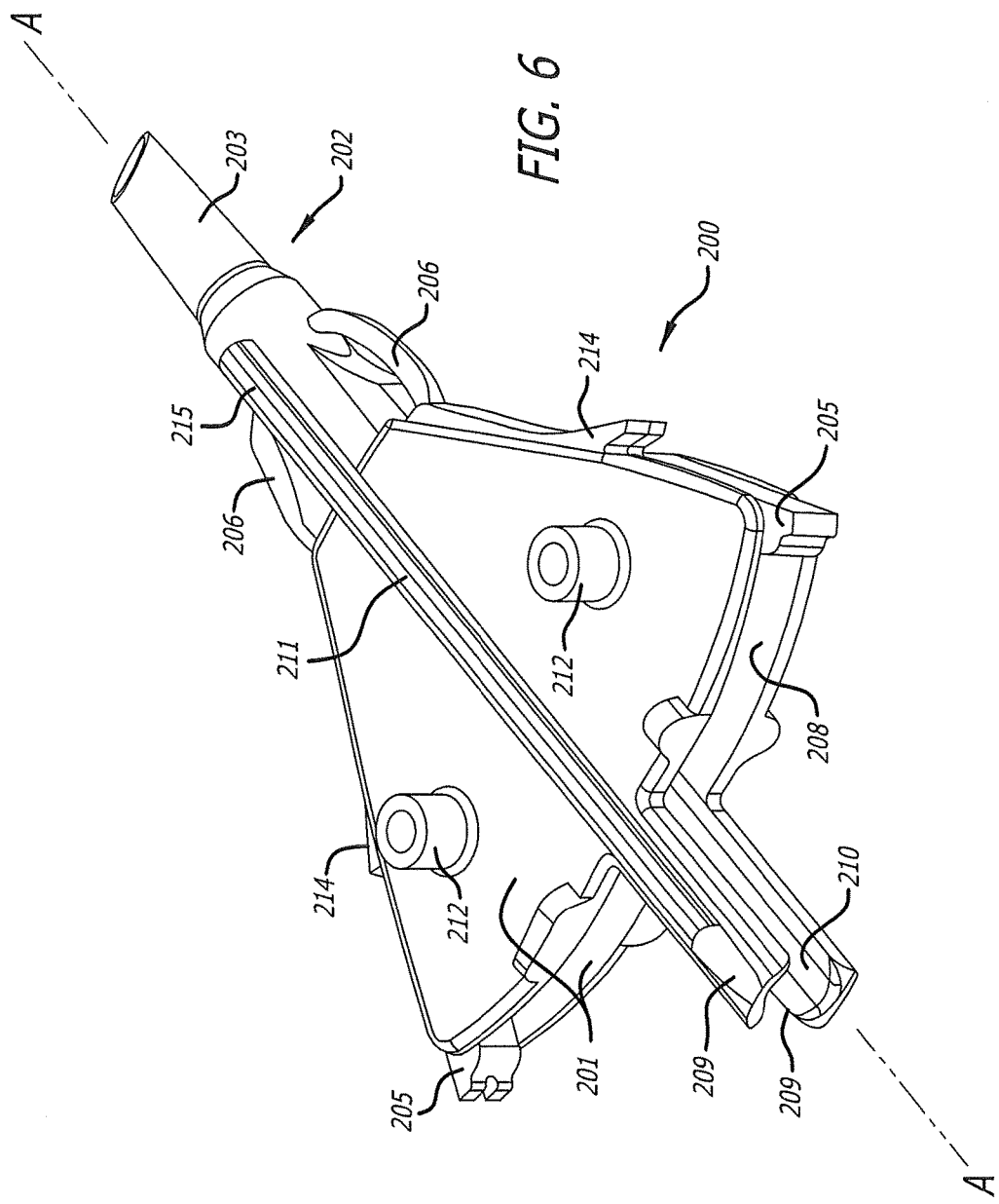
FIG. 6 is another isolated view of the lens support with the pair of folding members being pivotally mounted.

The lens support 200 according to one embodiment of the invention is represented in the perspective views of FIGS. 5 and 6. The lens support 200 comprises a pair of parallel wedge plates 201 of tapered shape and connected, at their narrow extremity, to an injection nozzle 202. The injection nozzle 202 is 15 terminated by a nozzle distal end 203 destined to be introduced in an incision formed in the wall of a patient's eye during lens replacement surgery. The interior of the injection nozzle 202 forms a nozzle canal 204. The lens support 200 also comprises a folding device for folding the lens 400 in a direction essentially perpendicular to the injector axis in response to axial movement of the plunger 2, as exemplified by the depictions of FIGS. 8 and 9. In the example of FIGS. 5 and 6, the folding device is a pair of folding members 205 being fixed by their distal extremity, which is the extremity on the side of the injection nozzle 202, to the external wall of the injection nozzle 202 with a flexible link 206. The folding members 205 comprise a notch 207 at their distal 25 extremity. The pair of folding members 205 can be pivotally mounted by abutting their respective notches 207 against edges of the injection nozzle 202, as shown in FIG. 6. The spacing between the two wedge plates 201 allows the folding members 205 to pivot within the two plates 201 while being guided laterally by the plates 201. When the two folding members 205 are in an open position as shown in FIG. 6, the two wedge plates 201 and the folding members 205 delimit an internal support cavity 208.

The wedges plates 201 also comprise a tail-shaped part 209, extending along the plunger 2 and within the plunger guide 300 as shown in FIG. 3. The internal surface of the tail-shaped part 209 forms a groove 210 extending along the injection axis A on the internal surface of the wedge plates 201, 5 forming an injection canal that extends the nozzle canal 204 of the injection nozzle 202. Two ribs 211 extend along the injection axis A, on the tail-shaped part 209 and the two opposite external surfaces of the wedge plates 201 of the lens support 200.

Figure 7A:
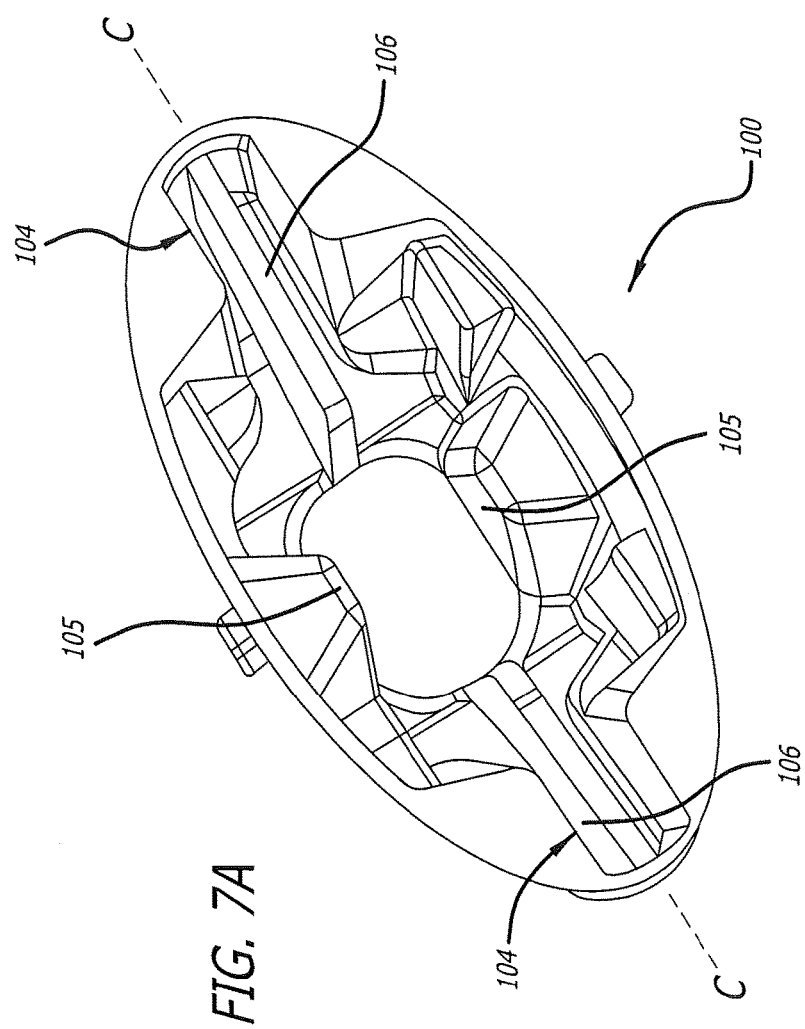
FIG. 7A is a perspective view of the lens support mounted within the support guide seen from the plunger side, according to an embodiment of the invention.
Figure 7B:
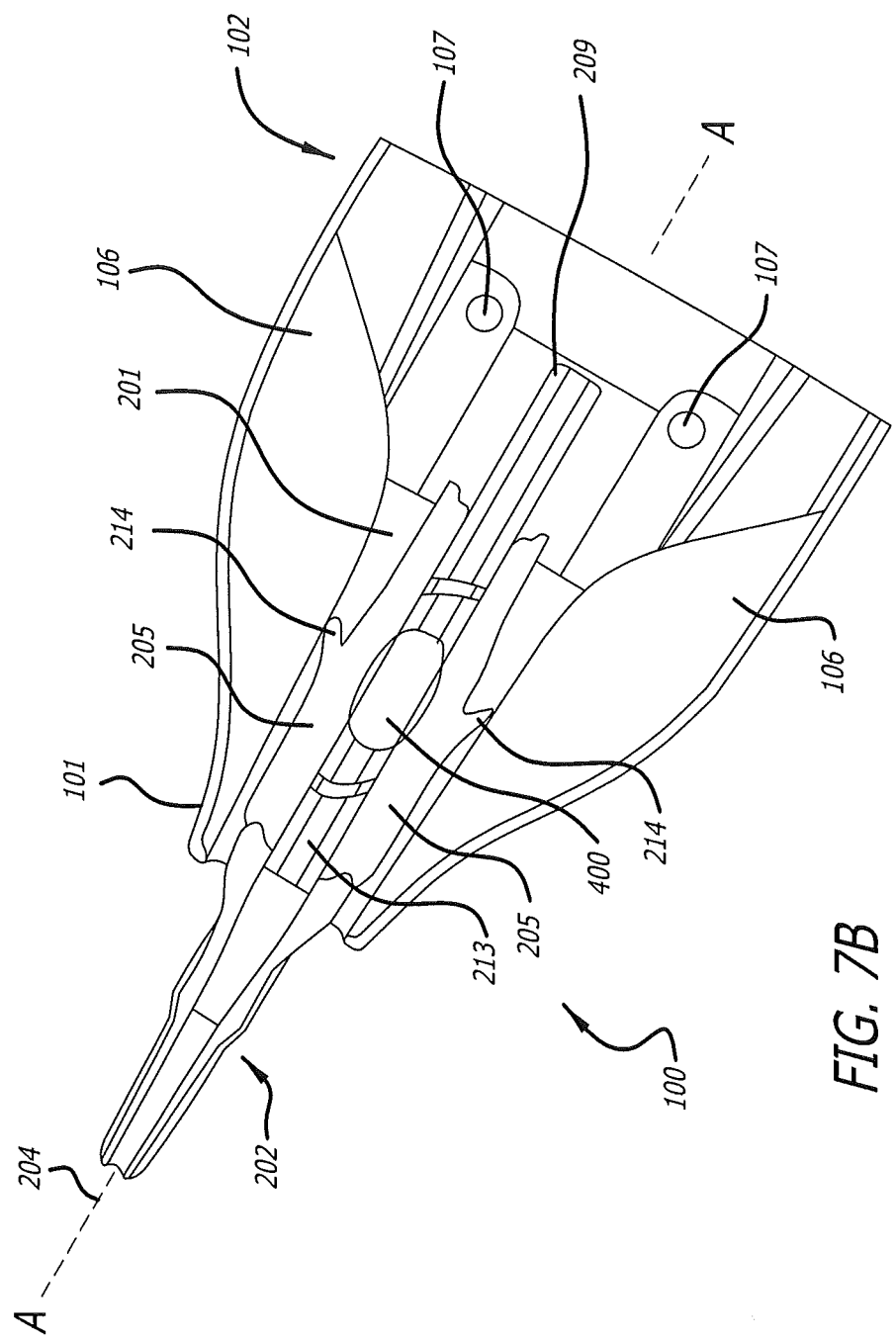
FIG. 7B is a sectional view taken along the line C-C of FIG. 7A.

FIGS. 7A and 7B depict a view of the support guide 100 according to an embodiment of the invention. In FIG. 7A, the support guide 100 is seen from the plunger side, and a section view along the line C-C of FIG. 7A is represented in FIG. 7B. In FIG. 7B, the lens support 200 is also shown with pivoted folding members 205.

The support guide 100 comprises two internal lateral sloped ridges 106, formed within the internal surface of the support guide 100 and sloping toward one another from the support guide proximal end 102 to the support guide distal end 101 of the support guide 100. These sloped ridges 106 are destined to cooperate with the folding members 205 as will be explained below.

In the example of FIGS. 7A and 7B, the internal surface of the support guide 100 also comprises two guiding slots 104 extending along both sides of the support guide 100, and adapted to guide laterally the movement of the lens support 200 within the support guide 100 along the injection axis A. The two ribs 211 press against two parallel guiding faces 105, extending along the injection axis A and oppositely disposed on the internal upper and lower surfaces of the support guide 100, in order to laterally guide the lens support 200 advancing within the support guide 100. Alternatively, the two ribs 211 can also press against two parallel guide ribs (not shown), extending along the injection axis A and oppositely disposed on the internal upper and lower surfaces of the support guide 100.

Other configurations of the support guide 100 are also possible. For example, the guiding slots 104 can be replaced by a pair of ribs in order to guide laterally the movement of the lens support 200 within the support guide 100 along the injection axis A.

The lens injectors of the present invention and their various parts may fabricated from different types of plastic materials. For example, the injector body may be produced from polycarbonate (PC), polyetherimide (PEI) or polysulfone (PSU), the end cap from PC, PEI or polyamide (PA), the plunger from PC, PEI or PSU, the support guide from PP, PC, polybutylene-terephtalate (PBT) or polyoxymethylene (PaM), the lens support from PaM, PP, BC, PA, PEI or polyethylene-terephtalate (PET), the plunger guide from PA, PBT or polypropylene, the plug from silicone or a vulcanized thermoplastic material, and the toric joints from silicone.

When assembling the injector 1, the end piece 6 and the toric joint seal 9 are first disposed on the proximal end of the plunger 2. Here, the plunger 2 is inserted into the end piece 6 through the opening 7. The plunger 2 is then inserted into the injector body 3. The two snap hooks 19 of the plunger 2 are arranged such as to be able to pass through the third portion 18 of the injector body 3, and abut against the distal end of portion 18 once the hooks 19 have passed this portion 18, preventing the plunger 2 from moving backward. Preferably, the end piece 6 is not yet clipped on the proximal end of the injector body 3.

In a preferred embodiment of the injector of the invention, a flexible 25 plug 20 is subsequently mounted on the distal end of plunger 22. The plug 20 is preferably made from a soft and flexible material, in order to avoid scratching of the lens 400 during the injection operation. Here, the distal end of the plunger 2 can comprise a forked distal end 22, as shown in FIG. 4, allowing the flexible plug 20 to extend at least partially in between the two teeth of the distal end 22. Other configurations of the distal end 22, that abuts the plug 20, are also possible. It is noted that plug 20 may be added to the plunger end 22 at a later stage, but prior to the mounting of the lens support 200 on the plunger guide 300.

The plunger guide 300 is next mounted within the injector body 3. The two opposite ribs 304 of the plunger guide 300 are guided within the corresponding grooves of the injector body 3 allowing the plunger guide 300 to be introduced into the desired angular position within the injector body 3. When the plunger guide 300 reaches its full rear position, it is forced into its closed position, the clipping means of the plunger 2, here the two snap hooks 19, are able to engage on the distal edge of the stop pieces 303, reversibly connecting the plunger guide 300 and the plunger 2.

The respective internal diameters of the portions 16, 17, 18 are such as to allow the plunger guide 300 to be introduced within the first and second portions but not within the third portion 18. The plunger guide 300 introduced within the injector body 3 from the flange 10 side thus abuts against the end of 15 the second portion 17, adjacent to the third portion 18. In this initial position, the plunger guide 300 extends along the first and second portions 16, 17. The internal diameter of the second portion 17 is such as to force the two opposite stop pieces 303 of the legs 301 to come in contact with the two snap hooks 19, the plunger guide 300 being thus in a closed position. When, in response to a forward movement of the plunger, the plunger guide is advanced out of the second portion 17 and into the first portion 16, the plunger guide 300 is able to regain its unstressed open position.

Other configurations of the injector body 3 are also possible, as long as they provide a configuration that enables the plunger guide 300 to be either in a closed position or in an unstressed open position, depending on the axial position of the plunger guide 300 within the injector body 3. For example, the injector body 3 can have a uniform internal diameter along its whole length but comprise internal ribs distributed around its internal wall, the ribs having a height that varies between sections along the injector body 3.

An intraocular lens 400 is then disposed unfolded between the two wedge plates 201, within the internal support cavity 208 (FIGS. 6 and 8). Preferably, the lens 400 is disposed within the internal support cavity 208 with the two haptics 401 of the lens being oriented along the injection axis A, as shown in FIG. 8.

The lens support 200 containing the lens 400 is then mounted on the plunger guide 300 by inserting the tail-shaped part 209 within the connecting portion 302 of the plunger guide 300 (FIGS. 3 and 6). In this position, the two folding members 205 are prevented from pivoting on the intraocular lens 400 by abutting against two protrusions 23 located on the flange 10 of the injector body 3 (FIG. 8). Also shown in FIG. 8 are two protruding members 21 arranged to maintain the unfolded lens 400 within the lens support 200 in its unfolded orientation as described above, until the lens 400 is folded and ejected. The protruding members 21 do not prevent the pivoting of the two folding members 205.

The support guide 100 is then fixed on flange 10 of the injector body 3 and the end cap 13 is placed over the injector, aligning seal holes 502 (FIG. 10) with seal posts or pins 500 (FIG. 11) and fastened to flange 10 using clamp 600 (FIG. 12) after placing the second toric joint seal 11 around the external periphery of the collar portion 12 (FIGS. 1 and 2).

The second toric joint seal 11 could also be placed at any other injector assembly steps, before the step of mating end cap 13 with the flange 10, described below.

In the case of a flexible hydrophilic intraocular lens, the end cap 13 and the injector body 3 are filled with an aqueous solution or fluid such as a saline solution, distilled water, or any other aqueous solution adequate for keeping the intraocular lens 400 wet. The aqueous solution may be introduced through filling openings, in the proximal end of the injector body 3 by means of a syringe.

The aqueous solution fills at least partly the volume enclosed by the end cap 13, lens support 200 and injector body 3. In the case a flexible hydrophobic intraocular lens is used, there is no need for a bathing solution or fluid such as saline and the step of filling the injector body 3 and the end cap 13 with an aqueous 30 solution may be omitted.

When the end cap 13 is fixed on the injector body 3, the lens support 200 abuts against the end cap 13 and the plunger 2 cannot be depressed.

Figure 15:
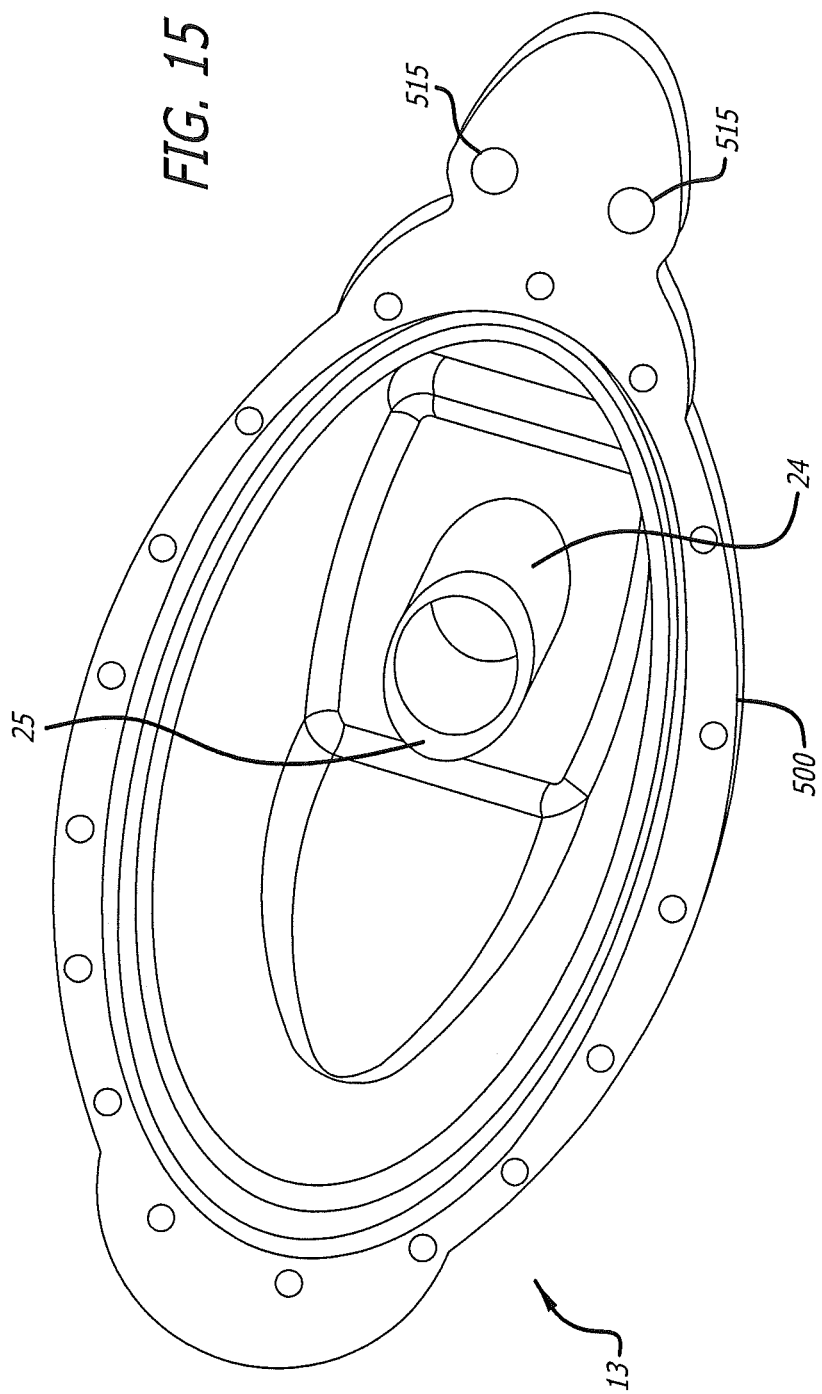
FIG. 15 is a top perspective view of an embodiment of an end cap, looking into the end cap from its proximal end.

In a preferred embodiment of the invention shown in see FIG. 15, end cap 13 comprises a central hollow tube 24 extending along the injection axis A toward the injector body 3. When the end cap 13 is fixed on the injector body 3, the distal end 215 of both opposite support ribs 211 of the lens support 200 abuts against the proximal end 25 of the central tube 24. In this configuration, the plunger 2 cannot be moved backward due to the snap hooks 19 abutting against the distal end of portion 18, as described above. Consequently, any false manipulation of the plunger 2 prior to the injection operation is avoided.

After fixing the end cap 13, the toric joint seal 9 is placed on a groove 26 on the proximal end of the injector body 3 (FIG. 9) and the end piece 6 is clipped on said proximal end, making the interior of the injector body sealed. The injector 1 is then ready to be packaged into a sealable flexible packaging (not) such as a sleeve, pouch or blister, or any other packaging. After the packaging is sealed, the packaged injector 1 is subjected to sterilization. A preferred method of sterilization is steam sterilization (autoclaving). In one alternative embodiment, the sleeve or pouch may be formed from a suitable foil material.

Prior to the injection operation, the injector is separated from its packaging, clamp 600 is removed and the end cap 13 is separated and removed from the flange 10, causing the aqueous solution to drain from the injector body 3 and the lens support 200. In order to keep the lens 400 and lens support 200 lubricated during the injection operation, a viscoelastic solution such as a solution containing hyaluronic acid, chondroitin sulfate or a cellulose derivative such as hydroxypropylmethylcellulose (HPMC) can be introduced within the internal support cavity 208 through holes 212 provided in the wedge plates 205 and the corresponding holes 107 of the support guide 100, for example, by using a syringe. Alternatively or in addition, the viscoelastic solution can also be introduced through the nozzle distal end 203 of the injection nozzle 202. The holes 107 and 212, and the nozzle distal end 203 also increase the fluidic communication within the end cap 13, facilitating the penetration of aqueous wetting solution into the lens support 200.

During an injection operation, the plunger 2 is depressed causing the plunger guide 300 to move forward over a first distance, advancing the lens support 200 within the support guide 100 along the injection axis A. During the advance of the lens support 200, the sloped ridges 106 of the support guide 100 force the pair of folding members 205 to pivot toward the injection axis A, drawing them near to one another until they become essentially parallel to the injection axis A, transforming the internal support cavity 208 into an injection canal 213 that extends along the folded folding members 205 and into the nozzle canal 204 of the injection nozzle 202. The lens support 200 advances in the support guide 100 until it abuts against the support guide 100 and cannot advance further.

Alternatively, the advance of the lens support 200 within the support guide 100, the folding members 205 of the lens support 200 may interact with the internal tapered side walls, forcing the folding members 205 to pivot inward and fold the intraocular lens in a direction essentially perpendicular to the injection axis A.

The above operation causes the intraocular lens 400 to fold, the lens 400 being folded or rolled in a direction essentially perpendicular to the injection axis A as shown in FIG. 7B, when completely folded. Consequently, the folded lens 400 is ready to be advanced axially into the nozzle canal 204.

In one embodiment of the invention, each folding member 205 comprises a protruding element 214. When the lens support 200 advances within the support guide 100, the sloped ridges 106 press against the protruding elements 214, and pivots the pair of folding members 205 toward the injection axis A, as described above. The protruding elements 214 can advantageously enhance the angular distance the folding members 205 will travel within the lens support 200 during the forward motion of the lens support within the support guide 100. Moreover, the use of protruding elements 214 can also reduce the friction during the advancement of the lens support 200 within the support guide 100, compared to a contact made along the whole folding member 205.

When the plunger 2 has moved over the first distance and the lens support 200 reached its abutting position within the support guide 100, the plunger guide 300 has moved completely outside the second portion 17 and extends only within the first portion 16 of the injector body 3 and within the support guide 100. It is noted that once plunger guide 300 has moved outside of second portion 17, it cannot be returned to its initial position within portion 17, thereby preventing an unfolding of the folded lens as a consequence of an accidental retraction of plunger 2. The diameter of the first portion 16 is large enough to allow the two legs 301 of the plunger guide 300 to regain their unstressed position, in which the two legs 301 are slightly bent apart, enabling the plunger guide 300 to be detached from the plunger 2, allowing the plunger 2 to move freely within the plunger guide 300 and advance within it.

Figure 9:
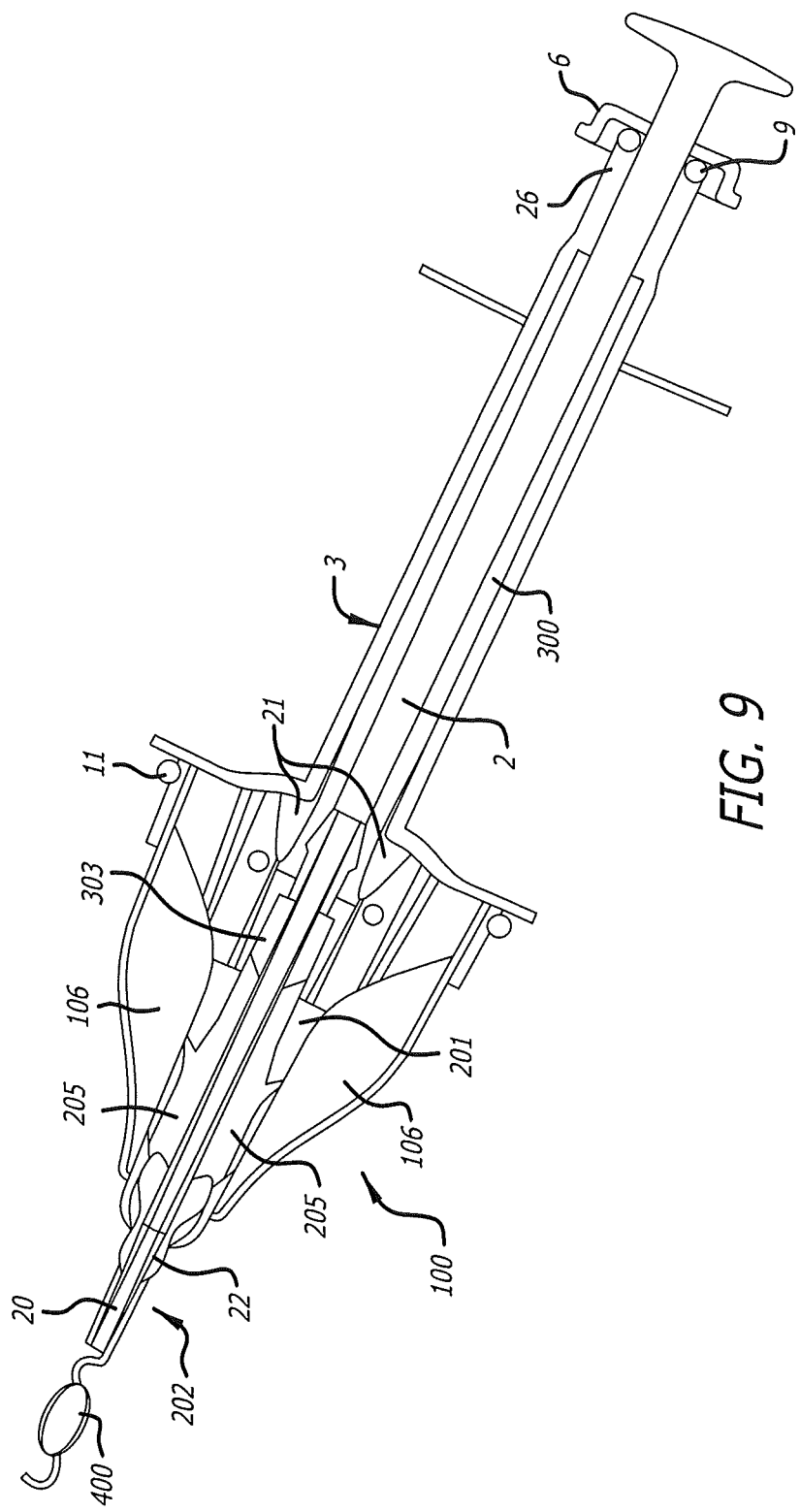
FIG. 9 illustrates the intraocular lens being completely folded within the lens support, according to an embodiment of the invention.

When operator pressure continues to be applied, the plunger 2 and plug 20 advance over a second distance and propel the folded lens 400 along the injection canal 213, and outside the nozzle distal end 203, enabling the lens 400 to be injected into the patient's eye (FIG. 9). The flexible plug 20 is able to follow conformably the varying dimensions of the internal support cavity 208 formed by the two folding members 205 and the nozzle canal 204, avoiding the necessity of requiring accurate dimensions for the different parts forming the compressed support cavity 208 and the nozzle canal 204.

In an exemplary embodiment of the invention, the lens support 200 is able to advance in the support guide 100 over a distance of about 15 mm, this distance corresponding to the length of the second portion 17 of the injector body 3. Here, the total length formed by the first and second portions 16, 17 corresponds essentially to the length of the plunger guide 300.

In one embodiment of the invention, the lens support 200, comprising the two wedge plates 201, the injection nozzle 202, the two folding, members 205 and links 206, is fabricated in one piece by an injection plastic molding process.

Modification to Improve Lubricity

As discussed previously, the above identified embodiments of an IOL injector typically require an additive or modification to improve the lubricity of the interior of the injector so as to prevent damage to the IOL or other implantable device and to facilitate implantation of the IOL or implantable device. The various embodiments of the system and method described herein are particularly advantageous in that they provide an injector having inherent lubricity without the addition of a separate coating and that can be steam sterilized in the presence of water without losing lubricious or dimensional properties. Moreover, while a specific design of injector is described above, the embodiments to be discussed below may be used with any design of injector, provided that the base material used to form the injector is amenable to the modifications described.

In one embodiment, the surface of the injector is modified by forming an inorganic-organic hybrid surface layer by reacting the surface of the injector with an ionic Lewis acid ionic solution using a suitable metal catalyst, such as, for example, but not limited to, magnesium II (Mg(II)), aluminum III (AL(III)) or the like. The inventors have found that a Mg(II) complex adduct can be bonded to the surface of the an injector in such a manner as to increase the hydrophilicity of the surface, while also increasing lubricity of the surface. Such a surface modification has been found to be stable over long periods of time when exposed to balanced saline solution, and to be able to stand up to steam sterilization. The method has also been found to be compatible with using different solvent-solute complexes, temperature and catalyst concentration, and steps to activate the surface of the injector.

In one embodiment, a Mg(II) ion catalytic process is used, and is particularly advantageous in that such a complex has a low toxicity in the eye. Inorganic hybrid coatings, such as the coatings described herein, not only increase wettability for forming chemical bonds between the polymer and the coating, but also decrease the coefficient of friction of the base polymer material when the coated polymer is immersed in an aqueous solution.

The main reaction of the carbonyl group are nucleophilic additions to the carbon-oxygen double bond. As shown in FIG. 16, this addition consists of adding a nucleophile and a hydrogen across the carbon-oxygen double bond.

Due to differences in electronegativity's, the carbonyl group is polarized. The carbon atom has a partial positive charge, and the oxygen atom has a partially negative charge.

There is a fundamental relationship between the mechanisms of the reactions at the carbonyl group introduced so far. In each case, a nucleophile or Lewis base attacks the positive end of the carbonyl group. And, in each case, the rate of reaction can be increased by coordinating a Lewis acid or electrophile at the other end of the carbonyl group The steps of the chemical process involved is as follows:

For a Lewis Acid-Base surface reaction, the activation/complex formation is as follows:

$$A + :B \rightarrow A-B \qquad \text{Equ. 1:}$$

Displacement reactions and partial de-polymerization of the polycarbonate molecules produce oligomers:

$$H[-OC_6H_4C(CH_3)_2CC_6H_4OCO-]_n + H_3O^+ \rightarrow_{Ionic\ liquid} H[-OC_6H_4C(CH_3)_2CC_6H_4OCO]_m OC_6H_4C(CH_3)_2CC_6H_4OH + H_2O + CO_2 \qquad \text{Equ. 2:}$$

$$H[-OC_6H_4C(CH_3)_2CC_6H_4OCO-]_n + 2CH_3OH \rightarrow_{Ionic\ liquid} H[-OC_6H_4C(CH_3)_2CC_6H_4OCO]_m OC_6H_4C(CH_3)_2CC_6H_4OH + (H_2CO)CO(OCH_3) \qquad \text{Equ. 3:}$$

Thus:

$$B-A+:B' \rightarrow B: + A-B' \qquad \text{Equ. 4:}$$

For double displacement:

$$A-B + A'-B' \rightarrow A-B' + A'-B \qquad \text{Equ. 5:}$$

The polymerization of aqua ions to polycation layers is regulated by the pH range of the solution. Thus, activating the polycarbonate and reacting it with a metallic Lewis acid solution such as $MgCl_2$ yields:

$$[Mg(H_2O)_6]^{2+}(aq) + (2+n)H_2O(l) \rightarrow Mg(OH)_{2n}H_2O(s) + 2H_3O+(aq) \qquad \text{Equ. 6:}$$

Note, the solubility in water of is given by:

$$K_{sp} = [Mg^{++}][OH^-]^2 \times 1.5 \times 10^{-11} \qquad \text{Equ. 7:}$$

$$H_2O(s)Mg(OH)_{2n}[-OC_6H_4C(CH_3)_2CC_6H_4OCO]_m OC_6H_4C(CH_3)_2CC_6H_4OMg(OH)_{2n}H_2O(s) \qquad \text{Equ. 8:}$$

The following is an exemplary process that can be used to modify the surface of a polycarbonate material, such as is used to form a lens injector body. Using this process, it is possible to form an ultrathin coating, on the order of one micron or less, on the surface of the polycarbonate construct. This coating, as described above, increases the hydrophilicity of the polycarbonate construct, resulting in increased lubricity of the surface of the construct, which assists in preventing damage to an intraocular lens that is pushed through the construct.

In general, the process includes three steps: 1) surface activation of the polycarbonate construct, which in this case may be a lens injector/cartridge assembly; 2) coating the surface of the polycarbonate construct; and 3) quenching and stabilizing the coated surface so as to provide a relatively permanent, modified surface having increased hydrophilicity and lubricity.

The activation process is carried out by placing one or more dry polycarbonate constructs, such as an intraocular lens cartridge or injector assembly into a reactor. The reactor will typically be heated for 0.5 to 2 hours at a temperature of 80 to 90 degrees centigrade to ensure that the constructs are dry. The reactor may be a glass reactor, which is placed into a temperature controlled oven, which may be a convection oven.

A solvent, such as, for example, 100% anhydrous Ethanol, Methanol mixed 10% w/w/ with anhydrous Ethanol, 100% anhydrous Ethanol mixed with $MgCl_2$ 1% w/w, or methanol mixed 10% w/w with a solution of anhydrous Ethanol mixed 1% w/w with $MgCl_2$, warmed to around 50 to 60 degrees centigrade, is added to the reactor containing the constructs. It will be apparent to those skilled in the art that other dry alcohols may be used without departing from the principles of the present invention.

The reactor is closed and then heated to a temperature between 40 degrees Celsius to 79 degrees Celsius for 30 minutes to 5 hours. While being heated, the reactor is rotated at 40-150 RPM. After the activation step is completed, the construct is dried. In one embodiment, the construct may be placed in a centrifuge to facilitate the drying process.

Once dried, the construct is then placed into another reactor for the coating process, where it is immersed in a freshly made solution of $MgCl_2$ (≥98% Ms=95.2) in DI water. The concentration of this solution may be in the range of 0.5 molal to 20 molal $MgCl_2$:DI water. The reactor is then heated to between 80 degrees Celsius to 131 degrees Celsius for 30 minutes to 5 hours. The reactor is rotated between 40-150 RPM. Once the coating process is complete, the construct is removed from the reactor and dried. In one embodiment, the construct is placed in a centrifuge for between 1 minute and 5 minutes at 150-350 RPM to facilitate the drying process.

The temperature of the coating process may vary as a function of the molality of the $MgCl_2$ solution, the boiling point of the solution, and the glass transition temperature Tg of the material from which the construct is formed.

While the above surface treatment process has been described with reference to use of $MgCl_2$, other entities may be used. For example, $Mg(OH)_2$, MgO, or Mg metal may be dispersed in water. $MgCl_2$ is added to a solution of $Mg(OH)_2$, a solution of MgO or a solution of $Mg(OH)_2$ plus Mg (metal) plus water to give a solution of Mg(OH)Cl, which is a highly active heterogeneous catalyst.

The surface species at this stage of the treatment process are mainly $[Mg(OH)_2]n$ and $[MgOH(x)Cl(y)]n$ attached to the polycarbonate substrate through —Mg—O— bridges coexisting with magnesium hydroxide, which deprotonates the hydroxyl phenol groups on the end of polycarbonate oligomer. As discussed below, the interfacial interaction becomes more pronounced when the pH quench solution is slightly basic, that is, having a pH greater than 7 with the presence Mg++ ions.

The dried, coated, construct is then placed into a quench vessel and is immersed in purified water having a pH adjusted to between 7.2-9.5 using NaOH as needed. The purified water may be balanced saline or water for injection having a composition by weight of the following components:

| | |
|---|---|
| Sodium Chloride | 0.64% |
| Potassium Chloride | 0.075% |
| Calcium Chloride Dihydrate | 0.048% |
| Magnesium Chloride Hexahydrate | 0.03% |
| Sodium Acetate Trihydrate | 0.39% |
| Sodium Citrate Dihydrate | 0.17% |

After the vessel containing the coated construct is filled with the quenching solution, the vessel is sealed and autoclaved for 1-3 hours at 121 degrees Celsius.

EXAMPLE 1

A polycarbonate construct, in this case a lens cartridge, was placed into a reactor and immersed in 100% anhydrous Ethanol. The reactor was heated to 60 degrees Celsius for 45 minutes. The construct was dried, and then placed into the coating reactor, which was filled with 2.0 molal solution of $MgCl_2$ in DI water. The reactor was maintained at a temperature of 80 degrees Celsius for one hour, the reactor being rotated at 120 RPM. After one hour, the construct was removed from the coating solution and dried in a centrifuge spinning at 120 RPM. The dried, coated construct was then placed in an autoclave vessel filled with a quench solution as described above, having a pH adjusted to 8.6-8.7, and autoclaved for two hours. The quenched, coated construct was observed to have increased hydrophilicity and improved lubricity.

EXAMPLE 2

A polycarbonate construct, in this case a lens cartridge, was placed into a reactor and immersed in 100% anhydrous Ethanol. The reactor was heated to 55 degrees Celsius for 35 minutes. The construct was dried, and then placed into the coating reactor, which was filled with 2.0 molal solution of $MgCl_2$ in DI water. The reactor was maintained at a temperature of 112 degrees Celsius for 65 minutes, the reactor being rotated at 120 RPM. After one hour, the construct was removed from the coating solution and dried in a centrifuge spinning at 120 RPM. The dried, coated construct was then placed in an autoclave vessel filled with a quench solution as described above, having a pH adjusted to 7.9-8.5, and autoclaved at a temperature of 121 to 123 degrees Celsius for two hours. The quenched, coated construct was observed to have increased hydrophilicity and improved lubricity.

EXAMPLE 3

A polycarbonate construct, in this case a lens cartridge, was placed into a reactor and immersed in 100% anhydrous Ethanol. The reactor was heated to 55 degrees Celsius for 35 minutes. The construct was dried, and then placed into the coating reactor, which was filled with a 2.0 molal solution of $AlCl_3$ in DI water. The reactor was maintained at a temperature of 112 degrees Celsius for 65 minutes, the reactor being rotated at 120 RPM. After one hour, the construct was removed from the coating solution and dried in a centrifuge spinning at 120 RPM. The dried, coated construct was then placed in an autoclave vessel filled with a quench solution as described above, having a pH adjusted to 7.9-8.5, and autoclaved at a temperature of 121 to 123 degrees Celsius for two hours. The quenched, coated construct was observed to have increased hydrophilicity and improved lubricity.

While several particular forms of the invention have been illustrated and described, it will be apparent that various modifications can be made without departing from the spirit and scope of the invention.

We claim:

1. A method for forming a wettable inorganic-organic hybrid coating on the surface of a polycarbonate construct to improve the lubricity of the surface of the polycarbonate construct, comprising:
    activating the surface of a polycarbonate construct by placing the construct in an activation solution and heating the solution at a selected activation temperature for a selected activation time;
    drying the activated construct;
    coating the activated construct by immersing the construct in a coating solution and heating the solution at a selected coating temperature for a selected coating time to form an inorganic hybrid coating on the surface of the construct;
    drying the coated construct; and
    quenching the coated construct by immersing the coated construct in a quenching solution contained within an autoclavable vessel and autoclaving the coated construct for a selected autoclaving time at a selected autoclaving temperature, the surface of the quenched coated construct having increased wettability and a decreased coefficient of friction compared to the wettability and coefficient of friction of an uncoated surface of a polycarbonate construct.

2. The method of claim 1, wherein the activation solution is 100% anhydrous Ethanol.

3. The method of claim 1, wherein the coating solution is a 2.0 molal solution of $MgCl_2$ in DI water.

4. The method of claim 1, wherein the quenching solution is balanced saline solution with a pH of 7.9-8.5.

5. The method of claim 1, wherein the coating solution is an ionic Lewis acid solution.

6. The method of claim 5, wherein the coating solution includes a metal catalyst.

7. The method of claim 1, wherein the polycarbonate construct is a cartridge configured to hold an intraocular lens.

8. The method of claim 1, wherein the polycarbonate construct includes a lens holding portion of an injector configured to deliver an intraocular lens into an eye.

* * * * *